United States Patent [19]

Sato et al.

[11] Patent Number: 4,690,819

[45] Date of Patent: Sep. 1, 1987

[54] METHOD FOR STABILIZING RUBELLA HA ANTIGEN

[75] Inventors: Akihiko Sato; Akira Noto; Fumiaki Morita, all of Osaka; Kunihiro Nakajima, Nara, all of Japan

[73] Assignee: Shionogi & Co., Ltd., Osaka, Japan

[21] Appl. No.: 792,316

[22] Filed: Oct. 28, 1985

[30] Foreign Application Priority Data

Dec. 14, 1984 [JP] Japan .................................. 59-264863

[51] Int. Cl.$^4$ .............................................. A61K 39/00
[52] U.S. Cl. ........................................ 424/88; 424/89; 530/412
[58] Field of Search ..................................... 424/88, 89

[56] References Cited

U.S. PATENT DOCUMENTS 3,553,312  1/1971  Delgado .................................. 424/89
4,195,074  3/1980  Safford .................................... 424/89
4,590,156  5/1986  Dorsett .................................... 424/89

OTHER PUBLICATIONS

Chong et al., "Purification of Biologically Active Rubella Virus Antigen . . . Chromatography" *J. Virol. Methods* 10 (1985) pp. 261–268.

*Primary Examiner*—Morton Foelak
*Assistant Examiner*—Garnette Draper
*Attorney, Agent, or Firm*—Birch, Stewart, Kolasch & Birch

[57] ABSTRACT

A method for stabilizing rubella HA antigen which comprises adjusting a rubella HA antigen suspension at pH 9.6 or higher, and more preferably, concurrently adding sodium azide thereto, or adding sodium azide alone at a concentration of 1 to 10% (w/v) thereto without the above adjustment of pH.

8 Claims, 3 Drawing Figures

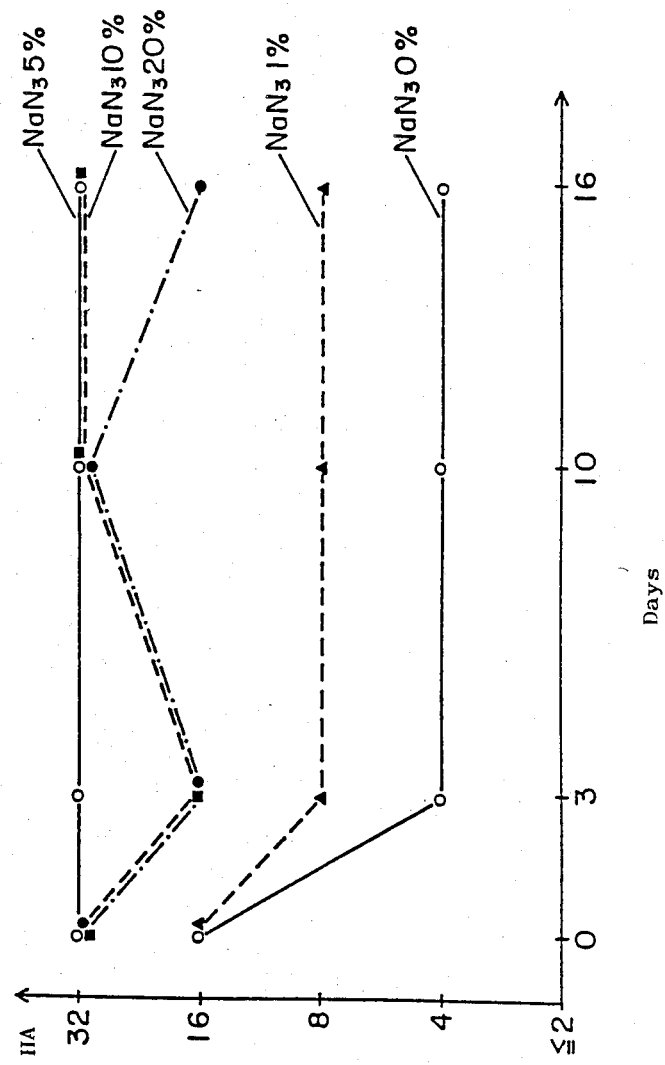

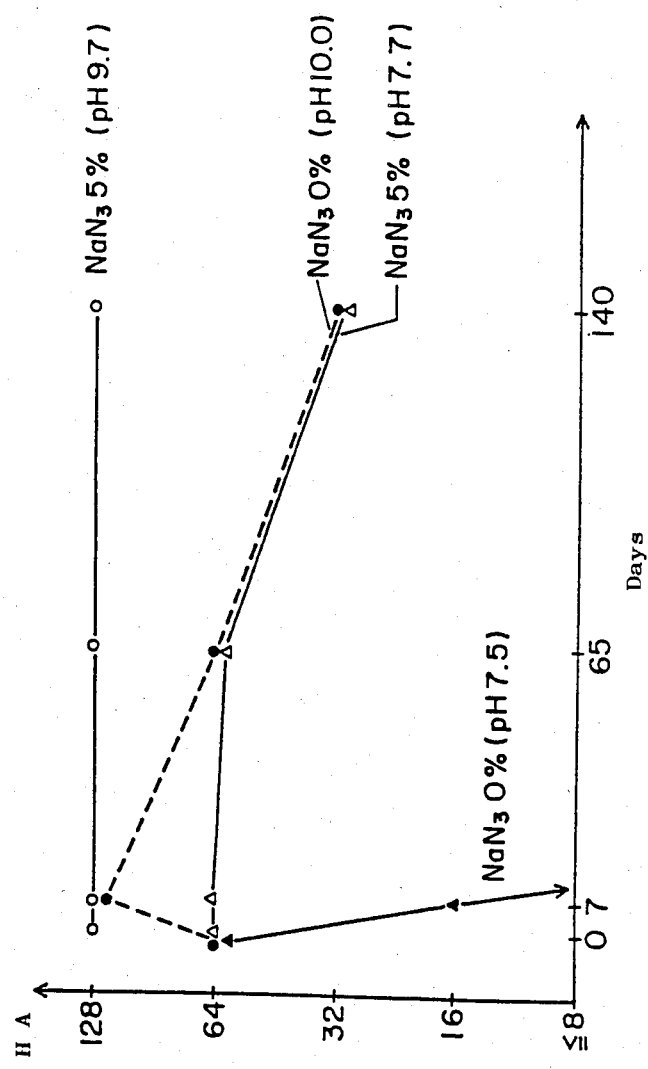

METHOD FOR STABILIZING RUBELLA HA ANTIGEN

BACKGROUND OF THE INVENTION

1. Field of the Invention

A certain kind of virus carries a component called HA antigen (Hemagglutination Antigen), which has a property agglutinating the animal erythrocytes, on their particle surface. Anti-virus antibodies inhibit the agglutination between the HA antigens and the animal erythrocytes. An anti-virus antibody titer can be determined by the Hemagglutination Inhibition (HI) test utilizing such a property of HA antigen.

Of the clinical tests for various viruses, the most general one is determination of antibody titer against rubella virus; and the HI test is generally used as serological method for diagnosing an infection or anamnetic infection with rubella virus. Particularly, rubella infection in the first pregnant stage is a matter of primary concern for pregnant women in a delivery stage as it causes a birth of congenital rubella child, so that the rubella HI antibody titer test has widely been applied as one of screening tests for pregnant women.

This invention relates to a method for stabilizing rubella HA antigen which is used in the rubella HI test based on the hemagglutination inhibition.

2. Prior Art

Rubella HA antigen is used in the rubella HI antibody titer test practiced generally. Rubella HA antigen suspension is desired to be stable without deterioration of antigen titer over a long term for simplifying a titer-adjusting procedure at the time of use and also for securing reproducibility of the data and accuracy of the test. And the stabilization prevents the waste of the reagent especially in dealing with a small number of samples. Therefore, various methods for keeping rubella HA antigen stable have been studied. For example, P. E. Halonen reported that rubella HA antigen which was extracted from the cells infected by rubella virus with a glycine buffer (pH 9.0) was stable at 4° C. and −70° C. for a few weeks. [Proc. Soc. Exp. Biol. Med. 125, 162–167 (1967)]. It is advertised that commercially available rubella HA antigen (by Flow Co.) is stable at pH 9.0–9.5 at 4° C. for 24 hours, but unstable at the lower pH range. Addition of sodium azide as a sterilizer at a concentration of about 0.1% is also effective.

SUMMARY

A rubella HA antigen suspension can be stabilized by adjustment at pH 9.6 or higher, preferably pH 9.7 to 11.0 and more preferably about pH 10. In addition to the above pH adjustment, the rubella HA antigen suspension is further stabilized by addition of sodium azide at a concentration of 0.05–10% (w/v). Sodium azide acts bacteriostatically at a concentration of above 0.05% and as a stabilizer at a concentration above 1%. Sodium azide, alone, also stabilizes the suspension at a concentration of 1–10% (w/v) without the adjustment of pH.

BRIEF DESCRIPTION OF THE DRAWINGS

FIG. 2 shows the influence of concentration of sodium azide on stability of rubella antigen, and FIG. 3 shows the influence of pH range and concentration of sodium azide on stability of rubella antigen. In each figure the horizontal axis means the stored days and the vertical axis means rubella HA antigen titer.

DESCRIPTION OF THE PREFERRED EMBODIMENTS

Figure 1:
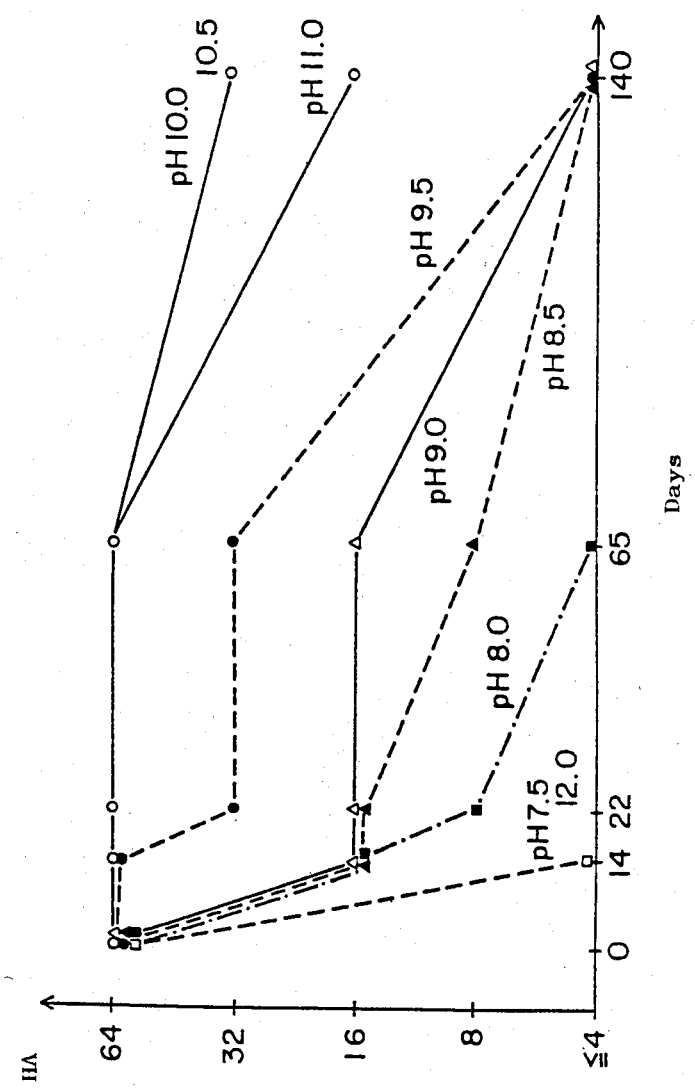
FIG. 1 shows the influence of pH range on stability of rubella antigen.

Various methods for stabilizing rubella HA antigen have been studied but such a method to fulfill the above requirements for stabilization has not yet been developed. The inventors of the present application first investigated the influence of pH of an antigen suspension on its stability in developing a longterm-stable rubella HA antigen suspension and elucidated that the rubella HA antigen suspension is not stable at a conventional pH range but more stable at higher pH. Moreover, in addition to about 0.1% of sodium azide added to the suspension in order to prevent the decrease of HA antigen titer by contamination of microorganisms during preservation, adjustment of pH and concurrent addition of an appropriate additional amount of sodium azide in such a way as noted above make the HA antigen stable synergistically.

A rubella HA antigen suspension can be stabilized by adjustment at pH 9.6 or higher, preferably pH 9.7 to 11.0 and more preferably about pH 10. This adjustment of pH can be achieved by using usual bases such as sodium hydroxide, potassium hydroxide, aluminium hydroxide and so on. The rubella HA antigen suspension may be lyophilized as necessary and the adjustment of pH may be carried out before or after lyophilization. The pH fixed before lyophilization does not alter after the regeneration of the lyophilized suspension and the suspension is kept stable. In addition to the pH adjustment, the rubella HA antigen suspension is further stabilized by addition of sodium azide at a concentration of 0.05–10% (w/v). Sodium azide acts bacteriostatically at a concentration of above 0.05% and as a stabilizer at a concentration at above 1%. Sodium azide alone also stabilizes the suspension at a concentration of 1–10% (w/v) without the adjustment of pH.

The rubella HA antigen suspension of the present invention is so stable that its antigen titer is not decreased over a long time, compared with conventional suspensions of the prior art. Since the pH and the addition of sodium azide in this invention do not influence any antibody titer in the rubella HI antibody titer test, the rubella HA antigen suspension of this invention can be used in the same manner as conventional suspensions.

The following examples are provided to illustrate the embodiment of this invention. They are not intended to limit the scope of the invention.

EXAMPLE 1

BHK-21 (Baby hamster kidney cells) are cultured in culture bottles and infected with rubella virus M-33 strain. After the infected cells are cultured at 37° C. for 3 to 7 days, the resulting culture medium is collected. The collected rubella HA antigen suspension (500 ml) is inactivated and adjusted to pH 10.0 with 2N-sodium hydroxide. The resulting precipitate is removed by filtration or centrifugation to give a rubella HA antigen suspension which exhibits pH 10. If required, the suspension is moved into and lyophilized in each vial at such a volume that, when the lyophilizate is dissolved with 2 ml/vial of purified water, the resulting suspension shows a titer of about 80 times.

The rubella HA antigen suspension showing pH above 9.6 is prepared and lyophilized in the same procedure as mentioned above.

EXAMPLE 2

To the suspension of rubella HA antigen (pH 10) prepared in Example 1 is added sodium azide in such a way that the sodium azide concentration is 0.1% (w/v) when the suspension is regenerated from the lyophilizate. Thus a pH 10 suspension of rubella HA antigen containing sodium azide is prepared. If necessary, the suspension is lyophilized in the same manner as mentioned in Example 1.

The suspension of rubella HA antigen of which the pH range is 9.6 or higher and the sodium azide concentration is between 0.05 and 10% (w/v) is prepared in the same procedure as mentioned above. The suspension may be lyophilized if necessary.

EXAMPLE 3

The rubella HA antigen suspension is collected in the same manner as mentioned in Example 1, and an appropriate amount of sodium azide is added thereto so as to show 1–10% (w/v) sodium azide concentration.

Method of Collection of Rubella HA Antigen

BHK-21 is cultured in a culture bottle, infected with a rubella virus M-33 strain and incubated at 37° C. On the 3rd to 7th day the cultured medium is collected, and the infectious virus is inactivated to give a rubella HA antigen suspension.

Method of Titration of Rubella HA Antigen (HA Titer)

Titration of rubella HA antigen is carried out according to the method of National Institute of Health Japan, that is, Veronal buffer [VBS(+)] containing 0.1% bovine serum-albumin (BSA) and 0.005% gelatin is used for diluent of serum and antigen. On a microtiter U-plate, the HA antigen is diluted by 2 fold serial dilution. Further 0.25% goose erythrocytes is added to the diluted antigen, and the mixture is well shaken, and allowed to stand in a refrigerator. The HA titer of the antigen is defined as the maximum dilution frequency causing complete hemagglutination after about an hour.

EXPERIMENT 1

To the collected rubella HA antigen was added 2N-sodium hydroxide to adjust the pH range at from 7.5 to 12. The stability of the HA titer was measured at each pH range of the antigen suspension stored at 4° C. The results are shown in Table 1. The antigen suspension adjusted to pH 10.0 showed no decrease in the titer for about 2 months, while the antigen suspensions adjusted to pH 9.5 or lower and to pH 12 were unstable.

EXPERIMENT 2

After the collected rubella HA antigen is lyophilized and suspended in purified water, the suspension is adjusted to pH 10.0 with 2N-sodium hydroxide and stored at 4° C. In this case the HA titer does not decrease for at least one month.

EXPERIMENT 3

The rubella HA antigen adjusted to pH 10.0 in Example 1 is lyophilized, suspended in purified water, and the suspension is stored at 4° C. In this case the HA titer does not decrease for at least 2 months.

EXPERIMENT 4

To the collected rubella HA antigen is added sodium azide at a concentration of 0–20% (w/v) and the suspensions are adjusted at a pH range of from 7.5 to 8.0 and stored at 4° C. The HA titer for each antigen suspension is measured. The results are shown in FIG. 2. In this case the suspensions are stable even at pH 7.5–8.0, at which the HA titer is easily decreased, for about 2 weeks when 5–10% of sodium azide is added. In addition, the suspensions containing 1–20% of sodium azide are more stable than the suspensions containing no sodium azide.

EXPERIMENT 5

The collected rubella HA antigen is adjusted to pH 10.0 or pH 7.5 with 2N-sodium hydroxide. Each antigen suspension is divided into two portions. Sodium azide is added to one portion at the concentration of 5%, but not to another portion. At this time, the pH range of the suspensions containing sodium azide are altered from 10.0 to 9.7 and from 7.5 to 7.7, respectively. These antigen suspensions are stored at 4° C. The HA titer of each suspension is measured and the results are shown on FIG. 3. The antigen suspension containing 5% sodium azide at pH 10.0 does not show any decrease of HA titer while stored at 4° C. for 140 days, and is more stable than the other stabilized antigen suspensions.

EXPERIMENT 6

The rubella HA antibody titer is measured with the stabilized HA antigen as mentioned above. HI antibody titration is carried out according to the method of National Institute of Health, Japan. The same instruments and reagents which are employed in the microtiter method for the HA titration are used. The maximum serum dilution frequency able to inhibit HA antigen is defined as the antibody titer. The results are shown in the following Table 1.

TABLE 1

| | Titration of HI antibody by the use of stabilized HA antigen | | |
|---|---|---|---|
| | Found values of rubella HI antibody titer | | |
| HA antigen suspension | *Controlled positive serum of patients (16 times) | *Controlled positive serum of patients (64-128 times) | *Controlled negative serum of patients (<8 times) |
| pH 9.0 | 16 | 128 | — |
| pH 10.0 | 16 | 128 | <8 |
| pH 11.0 | <8 | 32 | — |
| pH 12.0 | <8 | <8 | — |
| $NaN_3$ 5% | 16 | 64 | — |
| $NaN_3$ 10% | 16 | 64 | — |
| $NaN_3$ 20% | 8 | 64 | — |

TABLE 1-continued

| | Titration of HI antibody by the use of stabilized HA antigen | | |
|---|---|---|---|
| | Found values of rubella HI antibody titer | | |
| HA antigen suspension | *Controlled positive serum of patients (16 times) | *Controlled positive serum of patients (64-128 times) | *Controlled negative serum of patients (<8 times) |
| $NaN_3$ 30% | 8 | 32 | — |

*Controlled positive serum and negative serum of patients mean the serum of which the HI titer has been previously determined by the HI test using conventional HA antigen.

As shown in Table 1, HI antibodies show lower titer when the antigen suspension is adjusted at above pH 11, or when sodium azide is added at a concentration above 20%. But, when the stabilized antigen suspension is adjusted to its optimum pH of 10.0 and sodium azide is added at a concentration of 5%, there is no influence on HI antibody titer so that it can be used in the same manner as usual antigen.

As mentioned above, through the method of stabilization of rubella HA antigen in this invention, the antigens can be utilized effectively and waste of the can be prevented so that the test can be easily carried out in a laboratory dealing with a very small amount of sample and that the reproducibility and accuracy of the results can be secured.

What is claimed is:

1. A method for stabilizing inactivated rubella HA antigen which comprises adjusting an inactivated rubella HA antigen suspension at pH 9.6 or higher.

2. The method as claimed in claim 1, wherein the pH is fixed at 9.7 to 11.0.

3. The method as claimed in claim 1, wherein the pH is fixed at about 10.

4. The method as claimed in claim 1, wherein the rubella HA antigen suspension is adjusted at pH 9.6 or higher and sodium azide is added thereto.

5. The method as claimed in claim 4, wherein the sodium azide is added at a concentration of 0.05 to 10% (w/v).

6. A method for stabilizing inactivated rubella HA antigen which comprises adding sodium azide to an inactivated rubella HA antigen suspension at a concentration of 1 to 10% (w/v).

7. The method as claimed in claim 2, wherein the rubella HA antigen suspension is adjusted at pH 9.7 to 11 and sodium azide is added thereto.

8. The method as claimed in claim 3, wherein the pH of the rubella HA antigen suspension is fixed at about 10 and sodium azide is added thereto.

* * * * *